US00PP18674P2

(12) United States Plant Patent
Vandenberg

(10) Patent No.: US PP18,674 P2
(45) Date of Patent: Apr. 1, 2008

(54) ***CHRYSANTHEMUM* PLANT NAMED 'YOSALOON'**

(50) Latin Name: *Chrysanthemum×morifolium*
Varietal Denomination: Yosaloon

(75) Inventor: Cornelis P. Vandenberg, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 11/637,857

(22) Filed: Dec. 12, 2006

(51) Int. Cl.
*A01H 5/00* (2006.01)

(52) U.S. Cl. ..... Plt./290
(58) Field of Classification Search ..... Plt./287, Plt./290
See application file for complete search history.

*Primary Examiner*—Kent Bell
(74) *Attorney, Agent, or Firm*—C. A. Whealy

(57) ABSTRACT

A new and distinct cultivar of *Chrysanthemum* plant named 'Yosaloon', characterized by its upright plant habit; dark green-colored foliage; freely and uniformly flowering habit; decorative-type inflorescences; attractive two-tone orange bronze-colored ray florets; response time about 63 days; strong peduncles; and good postproduction longevity.

1 Drawing Sheet

Botanical designation: *Chrysanthemum×morifolium.*
Cultivar denomination: 'Yosaloon'.

BACKGROUND OF THE INVENTION

The present invention relates to a new and distinct cultivar of *Chrysanthemum* plant, botanically known as *Chrysanthemum×morifolium,* commercially grown as a cut flower and hereinafter referred to by the name 'Yosaloon'.

The new *Chrysanthemum* is a product of a planned breeding program conducted by the Inventor in Salinas, Calif. and Bogota, Colombia. The objective of the program is to create and develop new cut *Chrysanthemum* cultivars having inflorescences with desirable floret coloration and good inflorescence form and substance.

The new *Chrysanthemum* originated from a cross-pollination made by the Inventor in January, 2001, in Salinas, Calif. of a proprietary selection of *Chrysanthemum×morifolium* identified as code number T3502, not patented, as the female, or seed, parent with a proprietary selection of *Chrysanthemum×morifolium* identified as code number R326, not patented, as the male, or pollen, parent. The new *Chrysanthemum* was discovered and selected by the Inventor as a single flowering plant within the progeny of the stated cross-pollination in a controlled environment in Bogota, Colombia in June, 2002. The selection of this plant was based on its desirable ray floret color and good inflorescence form and substance.

Asexual reproduction of the new *Chrysanthemum* by terminal cuttings in a controlled environment in Bogota, Colombia since August, 2002, has shown that the unique features of this new *Chrysanthemum* are stable and reproduced true to type in successive generations.

SUMMARY OF THE INVENTION

Plants of the cultivar Yosaloon have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Yosaloon'. These characteristics in combination distinguish 'Yosaloon' as a new and distinct cultivar of *Chrysanthemum:*

1. Upright plant habit.
2. Dark green-colored foliage.
3. Freely and uniformly flowering habit.
4. Decorative-type inflorescences that are about 7 cm in diameter.
5. Attractive two-tone orange bronze-colored ray florets.
6. Response time about 63 days.
7. Strong peduncles.
8. Good postproduction longevity with inflorescences and foliage maintaining good substance and color for about two weeks in an interior environment.

Plants of the new *Chrysanthemum* differ from plants of the female parent selection in the following characteristics:

1. Plants of the new *Chrysanthemum* are taller than plants of the female parent selection.
2. Plants of the new *Chrysanthemum* are more freely flowering than plants of the female parent selection.
3. Plants of the new *Chrysanthemum* have longer peduncles than plants of the female parent selection.
4. Plants of the new *Chrysanthemum* and the female parent selection differ in ray floret color as plants of the female parent selection have light pink-colored ray florets.

Plants of the new *Chrysanthemum* differ from plants of the male parent selection in the following characteristics:

1. Plants of the new *Chrysanthemum* are more uniformly flowering than plants of the male parent selection.
2. Plants of the new *Chrysanthemum* flower earlier than plants of the male parent selection.
3. Plants of the new *Chrysanthemum* and the male parent selection differ in ray floret coloration as plants of the male parent selection have bright red-colored ray florets.

Plants of the new *Chrysanthemum* can be compared to plants of the *Chrysanthemum* cultivar Madera, disclosed in U.S. Plant Pat. No. 9,690. In side-by-side comparisons conducted in Bogota, Colombia, plants of the new *Chrysanthemum* differed from plants of the cultivar Madera in the following characteristics:

1. Plants of the new *Chrysanthemum* flowered much earlier and more uniformly than plants of the cultivar Madera.
2. Plants of the new *Chrysanthemum* had darker colored ray florets than plants of the cultivar Madera.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph at the top of the sheet comprises a side perspective view of a typical flowering stem of 'Yosaloon'.

The photograph at the bottom of the sheet comprises a close-up view of typical inflorescences of 'Yosaloon'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown in Bogota, Colombia during the summer in a polyethylene-covered greenhouse and under conditions and practices which approximate those generally used in commercial *Chrysanthemum* production. During the production of the cut flowers, day temperatures ranged from 20° C. to 25° C., night temperatures ranged from 4° C. to 9° C. and light levels ranged from 3,000 to 4,000 footcandles. Measurements and numerical values represent averages for typical flowering plants. The photographs and measurements were taken when plants were about two months old from planting.

Botanical classification: *Chrysanthemum×morifolium* cultivar Yosaloon.

Parentage:

*Female, or seed, parent.*—Proprietary selection of *Chrysanthemum×morifolium* identified as code number T3502, not patented.

*Male, or pollen, parent.*—Proprietary selection of *Chrysanthemum×morifolium* identified as code number R326, not patented.

Propagation:

*Type.*—Terminal vegetative cuttings.

*Time to initiate roots.*—About ten to 14 days with soil temperatures of about 18° C. to 21° C.

*Root description.*—Fine, fibrous; white in color.

*Rooting habit.*—Freely branching.

Plant description:

*Appearance.*—Herbaceous decorative-type cut flower.

*Flowering stem description.*—Aspect: Erect. Length: About 109 cm. Spray diameter: About 13.25 cm. Stem diameter: About 5 mm. Internode length: About 3.3 cm. Texture: Pubescent; longitudinally ridged. Color: 148B.

*Foliage description.*—Arrangement: Alternate; simple. Length: About 8 cm. Width: About 5 cm. Apex: Cuspidate. Base: Attenuate. Margin: Palmately lobed; irregularly serrate; sinuses parallel to slightly divergent. Texture, upper and lower surfaces: Pubescent; veins prominent on lower surface. Color: Developing and fully expanded foliage, upper surface: 147A; venation, 147C. Developing and fully expanded foliage, lower surface: 147B; venation, 147C. Petiole: Length: About 2.8 cm. Diameter: About 3 mm. Texture, upper and lower surfaces: Pubescent. Color, upper surface: 147C. Color, lower surface: 148C.

Inflorescence description:

*Appearance.*—Decorative-type inflorescence form with elongated oblong-shaped ray florets. Inflorescences borne on terminals, arising from leaf axils. Ray florets develop acropetally on a capitulum. Uniform flowering habit.

*Fragrance.*—Moderate; spicy.

*Flowering response.*—Under natural conditions, plant flower in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about 63 days later.

*Postproduction longevity.*—In an interior environment, inflorescences and foliage will maintain good color and substance for about two weeks in an interior environment.

*Quantity of inflorescences.*—Freely flowering habit, about seven inflorescences per stem develop.

*Inflorescence size.*—Diameter: About 7 cm. Depth (height): About 3.5 cm. Disc diameter: No disc florets observed. Receptacle diameter: About 2 cm. Receptacle height: About 1.1 cm.

*Inflorescence buds.*—Shape: Ovoid. Height: About 2 cm. Diameter: About 1.5 cm. Color: 173A.

*Ray florets.*—Shape: Elongated oblong to ligulate or quilled. Surface: Concave. Aspect: Initially incurved, with development, about 45° from vertical. Length: About 3.5 cm. Width: About 8 mm. Apex: Acute. Base: Fused. Texture: Smooth, glabrous; velvety; longitudinally ridged. Number of ray florets per inflorescence: About 205 arranged in about 18 whorls. Color: When opening, upper surface: 170A to 170B. When opening, lower surface: 172A. Fully opened, upper surface: 164B; color becoming closer to 163B with development. Fully opened, lower surface: 172D; color becoming closer to 167D with development.

*Phyllaries.*—Quantity per inflorescence/arrangement: About 24 arranged in about three whorls. Length: About 8 mm. Width: About 3 mm. Shape: Elliptic. Apex: Acute. Base: Truncate. Margin: Entire. Texture, upper surface: Smooth, glabrous. Texture, lower surface: Pubescent. Color, upper surface: Close to 146A. Color, lower surface: Close to 148A.

*Peduncles.*—Length: About 20.4 cm. Diameter: About 2 mm. Angle: About 20° to 30° from vertical. Strength: Strong. Texture: Pubescent; longitudinally ridged. Color: Close to 148A.

*Reproductive organs.*—Androecium: None observed. Gynoecium: Pistil length: About 5 mm. Stigma shape: Bi-parted. Stigma color: Close to 1B. Style length: About 2 mm. Style color: Close to 145B. Ovary color: Close to 157A.

*Seed/fruit.*—Seed and fruit production has not been observed.

Disease/pest resistance: Resistance to pathogens and pests common to *Chrysanthemums* has not been observed on plants grown under commercial conditions.

Temperature tolerance: Plants of the new *Chrysanthemum* have demonstrated good tolerance to low temperatures of about 4° C. and high temperatures of about 35° C.

It is claimed:

1. A new and distinct *Chrysanthemum* plant named 'Yosaloon' as illustrated and described.

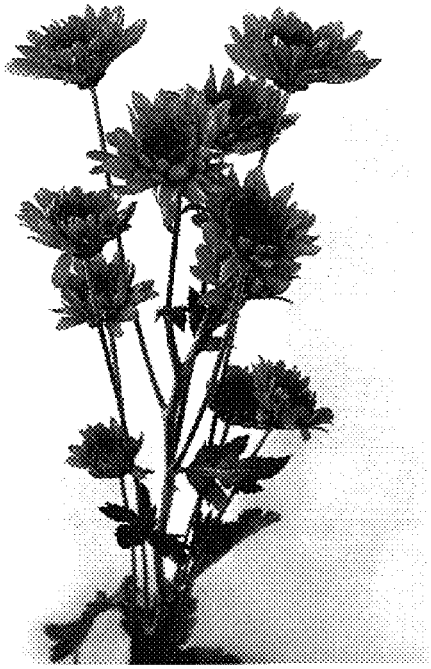
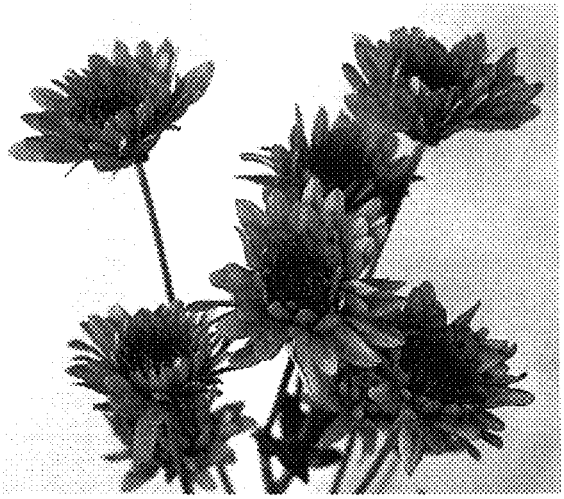

* * * * *